United States Patent [19]

Luenemann

[11] Patent Number: 5,006,338

[45] Date of Patent: Apr. 9, 1991

[54] WART TREATMENT

[76] Inventor: Brigitte Luenemann, Alter Fischmarkt 1, D-4400 Munster, Fed. Rep. of Germany

[21] Appl. No.: 156,628

[22] Filed: Feb. 17, 1988

[30] Foreign Application Priority Data

Feb. 18, 1987 [DE] Fed. Rep. of Germany ....... 3705151

[51] Int. Cl.$^5$ ...................... A61K 35/78; A61K 33/04
[52] U.S. Cl. ............................. 424/195.100; 424/714; 514/885
[58] Field of Search ...................... 424/195.1, 165, 714; 514/885

[56] References Cited

U.S. PATENT DOCUMENTS

| | | | |
|---|---|---|---|
| 104,146 | 6/1870 | Hare | 424/195.1 |
| 203,965 | 5/1878 | Wainwright | 424/195.1 |

FOREIGN PATENT DOCUMENTS

| | | | |
|---|---|---|---|
| 2551962 | 5/1977 | Fed. Rep. of Germany | 424/195.1 |
| 2296426 | 9/1976 | France | 424/165 |
| 2431863 | 3/1980 | France | 424/195.1 |

OTHER PUBLICATIONS

Homöopathisches Arzneibush, pp. 20–24, 348–350, 424–426 (1985).
Lust, *The Herb Book*, First Edition, pp. 93,98–99, 110–111, 137–139,155–156,180,265–266,275,299,3-54–355,374–375.

*Primary Examiner*—John W. Rollins
*Attorney, Agent, or Firm*—Pollock, Vande Sande & Priddy

[57] ABSTRACT

A wart treatment consists of a perorally administrable mixture of liquid dilutions (degree of dilution D2 to D6) of known phytopreparations which individually and/or collectively exhibit an immunostimulating effect. Preferably, at least a content of (a) 0.5 to 2 parts by weight of *Euphorbia cyparissias*, degree of dilution D3 to D6; (b) 0.5 to 2 parts by weight of *Clematis recta*, degree of dilution D2 to D4; and (c) 0.5 to 2 parts by weight of Mezereum, degree of dilution D2 to D4 is provided. In addition, one or several component(s) of the following group may selectively be provided, viz. (d) Ranunculus, degree of dilution D2 to D4; (e) *Veratrum album*, degree of dilution D3 to D6; (f) Aconitum, degree of dilution D3 to D6; (g) Arnica, degree of dilution D2 to D4; (h) *Atropa belladonna*, degree of dilution D3 to D6; (i) *Cinchona succiruba* (China), degree of dilution D2 to D4; (k) *Eucalyptus globulus*, degree of dilution D2 to D4; (l) Lycopodium, degree of dilution D3 to D6; *Nux vomica*, degree of dilution D3 to D6; and (n) sulfur, degree of dilution D4 to D6. The treatment is effective by stimulating the endogenous immunodefense mechanisms, wherein a controlled reaction against papillomaviruses is provoked.

16 Claims, No Drawings

WART TREATMENT

The present invention relates to a wart treatment composition, and in particular to a wart treatment composition substantially consisting of a mixture of liquid dilutions of known phytopreparations. Further, the present invention relates to the use of known phytopreparations for removing warts. It has been possible to prove the effectiveness of the novel wart remedy both in humans and animals.

Warts are transmitted by papillomaviruses. Until today, more than forty types of papillomaviruses have been characterized, which may cause different warts.

In most cases the development of warts is due to direct contact with virus particles. The risk of an infection depends not only on the amount and virulence of the virus particles but also on the patient's susceptibility and on the condition of the patient's skin environment. There are indications that warts are much more frequently contracted by patients whose endogenous immunity has been weakened.

The non-malignant wart diseases typically have a tendency to disappear spontaneously. Here, too, the causes which have not yet been clarified completely are assumed to reside in endogenous immunity mechanisms.

Except for the direct action of refrigeration, the removal with a sharp spoon or with the electrosurgical snare—warts have hitherto been exclusively treated by the application of locally acting treatments. Known locally applicable wart treatment compositions contain salicylic acid, possibly in combination with lactic acid, glacial acetic acid and/or fluorouracil; for application in persistent cases, wart remedies may also contain highly cytotoxic substances such as podophyllin.

Practice has shown that these known, locally applicable wart remedies do not always lead to satisfactory results. Partly the warts reappear after discontinuation of the therapy; even after repeated surgical removal, new warts may occur in the scar area. It is desirable precisely for such persistent cases to provide a wart treatment composition permitting treatment of warts through another therapeutic mechanism.

Based thereon, it is the object of the present present invention to provide a novel wart treatment composition.

The solution of this object as provided by the present invention is characterized by a perorally administrable wart treatment composition substantially consisting of a mixture of liquid dilutions (degree of dilution D2 to D6) of known phytopreparations which either individually or collectively have an immunostimulating effect.

Accordingly, by stimulating the endogenous immunity the present invention realizes a treatment of warts caused by papillomaviruses in humans and animals.

It has meanwhile been proven for a number of homeopathic phytopreparations that they may cause a non-specific stimulation of the immunologic system. This applies both to the cellular and to the humoral defence systems; see especially the essay "Immunstimulantien und Phytotherapeutika" by Professor Dr. H. Wagner, Munich, in Zeitschrift für Phytotherapie 7, pp. 91 to 98 (1986). At least part of the immunostimulating phytopreparations specified therein (see Table I) is also useful as an agent or adjuvant of the wart treatment composition according to the present invention. However, in this essay Professor Dr. H. Wagner does not refer to the treatment of warts by means of a perorally administrable remedy stimulating the immunologic system. Likewise, peroral treatment of warts has not yet been known from folk medicine.

Preferably, the wart treatment composition according to the present invention comprises known phytopreparations in the form of liquid dilutions.

A particularly preferred embodiment of a wart treatment composition according to the present invention is manufactured as a perorally administrable, pharmaceutic preparation and comprises at least (a) 0.5 to 2 parts by weight of *Euphorbia cyparissias*, degree of dilution D3 to D6;

(b) 0.5 to 2 parts by weight of *Clematis recta*, degree of dilution D2 to D4, and (c) 0.5 to 2 parts by weight of Mezereum, degree of dilution D2 to D4.

Mostly, the preparation was administered in a dose of approximately 10 to 20 drops at least three times a day. The period of administration ranged from ten days to four weeks. In a practice extending over several years a significant effect was observed in patients having vulgar warts which typically are attributable to human papillomaviruses (HPV) of type 1, 2, 3, 4 and 7. In many cases the patients had previously repeatedly been treated conservatively without success. After administration of the wart treatment composition according to the present invention within the mentioned period, the papillomatous hyperkeratoses dropped off without leaving any scars. Plantar warts on the foot soles and the like receded so that they disappeared entirely.

By means of the preparation according to the present invention a drug has been provided for the first time which does not only induce non-specific para-immunity but also provokes a controlled defensive reaction against papillomaviruses. The preparation according to the invention can compensate for immunodeficiencies; this is particularly important, because substantially no simple and inexpensive virostatic agents, especially against papillomaviruses, are available. In this connection, the veterinary field should also be considered; it has, for instance, been possible to remove persistent warts on horses by means of the wart treatment composition according to the present invention. Due to the extremely low dose, the administration of the wart treatment composition according to the present invention does not have undesired side effects.

The wart treatment composition according to the present invention should at least comprise the above-mentioned components (a), (b) and (c). This permits influencing of the specific immunodeficiency which—under the conditions of the virus infection—obviously caused the development of the warts. Besides, the wart treatment composition according to the present invention may additionally comprise one or several selective component(s). According to experience made so far an addition of these selective components increases and/or promotes the effect of the wart treatment composition according to the present invention. In particular, it is possible with these selective components favorably to influence a general immunosuppression which occurs frequently especially in adults. These selective components comprise in particular:

(d) 0.5 to 2 parts by weight of Ranunculus, degree of dilution D2 to D4;

(e) 0.5 to 2 parts by weight of *Veratrum album*, degree of dilution D3 to D6;

(f) 0.5 to 2 parts by weight of Aconitum, degree of dilution D3 to D6;

(g) 0.5 to 2 parts by weight of Arnica, degree of dilution D2 to D4.

For instance, an orally applicable wart treatment composition which has with great success been used within the scope of the present present invention is composed of:

(a) 0.5 to 2 parts by weight of *Euphorbia cyparissias*, degree of dilution D3 to D6;

(b) 0.5 to 2 parts by weight of Clematis, degree of dilution D2 to D4;

(c) 0.5 to 2 parts by weight of Mezereum, degree of dilution D2 to D4;

(d) 0.5 to 2 parts by weight of Ranunculus, degree of dilution D2 to D4;

(e) 0.5 to 2 parts by weight of *Veratrum album*, degree of dilution D3 to D6;

(f) 0.5 to 2 parts by weight of Aconitum, degree of dilution D3 to D6; and (g) 0.5 to 2 parts by weight of Arnica, degree of dilution D2 to D4.

By further modifying the present present invention, it has been found that in many cases certain further additives have an advantageous effect and may further increase the effectiveness of the wart treatment composition according to the invention. These further additives comprise:

(h) 0.5 to 2 parts by weight of *Atropa belladonna*, degree of dilution D3 to D6;

(i) 0.5 to 2 parts by weight of *Cinchona succiruba*, degree of dilution D2 to D4;

(k) 0.5 to 2 parts by weight of *Eucalyptus globulus*, degree of dilution D2 to D4;

(l) 0.5 to 2 parts by weight of Lycopodium, degree of dilution D3 to D6;

(m) 0.5 to 2 parts by weight of Nux vomica, degree of dilution D3 to D6; and (n) 0.5 to 2 parts by weight of sulfur, degree of dilution D4 to D6.

According to a further aspect the present invention concerns—also in the sense of a second indication—the use of known phytopreparations having an immunostimulating effect, especially and preferably the drug mixtures specified in the claims, for treating warts caused by papillomaviruses, in humans and animals. Here, the wart treatment composition is preferably manufactured for peroral application. The surprising effect of this application, viz. controlled provocation of endogenous defence reactions against the warts induced by papillomaviruses, is obviously based on a synergistic effect, for the effect of combination-type preparations is much greater than that of the individual components.

All components of the wart treatment according to the present invention are known, homeopathic or other drugs the preparation and potentiation of which to the desired degree of dilution is described in specialized literature. As far as the inventor knows, both the individual drugs and their mixtures have not yet been used for activating the endogenous immunity against papillomaviruses in order to provide a wart treatment. Although the mentioned drugs have been known, their preparation and dilution will briefly be explained below so as to ensure a complete, fully sufficient disclosure, wherein reference will especially be made to "Homöopathisches Arzneibuch", complete new edition 1985 published by "Deutscher Apotheker-Verlag, Stuttgart, and Govi-Verlag GmbH", Frankfurt.

Homöopathisches Arzneibuch" (homeopathic pharmacopoeia), is published by the order and supervision of the German Government (Ministry of Youth, Family and Health) and is an official document having a quasi-legal function.

The method of drying plants and to determine the loss of a sample on drying is described on page 2 thereof along the following lines:

LOSS DURING DRYING

Said loss during (by) drying is expressed in mass loss (percent by weight in grams) obtained by drying under the following conditions:

A weighing glass is previously dried at a temperature between 100° and 110° C. 2.00 to 5.00 grams of fine comminuted fresh plants or plant parts, which have been thoroughly weighed, are dried within said weighing glass for at least two hours and thereafter to a constant mass weight at a temperature between 100° and 110° C. After each drying step the obtained mass is allowed to cool to room temperature within an exsiccator device.

Unless specified otherwise, the original tinctures and the liquid decimal dilutions are prepared according to the following general specification:

The plants or plant parts are finely comminuted. The loss of a sample on drying is determined. The comminuted plant mass is immediately blended with 86% ethanol in an amount of at least half its weight and stored in sealed containers at a temperature not exceeding 20° C.

The amount of 86% ethanol ($A_3$) required for the plant mass is calculated according to the following formula $$A_3 = \frac{2 \times M \times T}{100} \text{ (kg)},$$

wherein

M is the weight of the plant mass in kg and

T is the loss of the sample on drying in %, the already added amount of ethanol is subtracted therefrom and the remainder is mixed with the batch. The phrase "the already added amount of ethanol is subtracted therefrom and the remainder is mixed with the batch" as discussed on pages 23 and 24 of "Homöopathisches Arzneibuch" has the following meaning:

A part of the fine comminuted fresh plants or plant parts is dried to determine the loss by weighing. To another part of the same fine comminuted fresh plants or plant parts is added ethanol (86%) in an amount of at least half the weight of the weight of the fresh plants or plant parts. The mixture of the fresh plants or plant parts and ethanol is maintained within a closed vessel at a temperature not exceeding 20° C. Thereafter the necessary amount of ethanol ($A_3$) in order to prepare an original tincture is determined according to the formula as given in lines 2,3 on page 8 of the specification (or page 24 of "Homöopathisches Arzneibuch"). From the calculated amount of ethanol ($A_3$) is deducted the amount of ethanol, which has been previously added to the fresh plants or plant parts. The residual calculated (from $A_3$) amount of ethanol is added to the mixture of fresh plants or plant parts and ethanol maintained in the vessel. The obtained batch, comprising the original mixture of fresh plants or plant parts and ethanol and the added amount of calculated residual ethanol is maintained for at least ten days at a temperature not exceeding 20° C. Gand is shakened repeatedly.

Thereafter, the mixture is squeezed and filtrated in order to obtain an original tincture. The batch is left for at least ten days at a temperature not exceeding 20° C. and shaken repeatedly. Thereafter, squeezing and filtration are performed.

Adjustment to a predetermined, desired decimal dilution (potentiation) is achieved according to the following specification:

The 1st decimal dilution (D1) is prepared from
3 parts of original tincture and
7 parts of 62% ethanol.

The 2nd decimal dilution (D2) is prepared from
1 part of the 1st decimal dilution and
9 parts of 62% ethanol.

The 3rd decimal dilution (D3) is prepared from
1 part of the 2nd decimal dilution and
9 parts of 62% ethanol.

The 4th decimal dilution (D4) is prepared from
1 part of the 3rd decimal dilution and
9 parts of 43% ethanol.

Higher decimal dilutions are prepared analogously with 43% ethanol.

The liquid drug dilutions which are specified below and all of which have been known can be obtained according to the above specification or according to a specification modified for an individual case.

(a) *Euphorbia cyparissias*, D4

For preparing the original tincture, the whole fresh, blossoming plant of *Euphorbia cyparissias L.* is used. The original tincture is a brownish-green to brownish-yellow liquid of indifferent smell and sharp to bitter taste. The relative density of the original tincture ranges from 0.895 g/cm$^3$ to 0.915 g/cm$^3$. The dry residue amounts to at least 1.6% and at most 3.4%.

(b) *Clematis recta*, D2

For preparing the original tincture, the fresh, aboveground parts of blossoming plants of *Clematis recta L.* are used. The original tincture is a brownish-green liquid having no special smell or taste. Its relative density ranges from 0.0900 g/cm$^3$ to 0.915 g/cm$^3$. The dry residue has to amount to at least 2.4%.

(c) Mezereum, D3

For preparing the original tincture, fresh twig bark of mezereon (*Daphne mezereum*) gathered before blossoming is used. The density of the original tincture ranges from 0.895 g/cm$^3$ to 0.910 g/cm$^3$. Its dry residue ranges from 2 to 4%.

(d) *Ranunculus bulbosus*, D3

For preparing the original tincture, the whole fresh, blossoming plant of *Ranunculus bulbosus L.* is used. The original tincture is a greenish-yellow to yellowish-brown liquid having no special smell. Its relative density ranges from 0.900 g/cm$^3$ to 0.915 g/cm$^3$. The dry residue amounts to at least 1.5% and at most 3.0%.

(e) *Veratrum album*, D4

The original tincture is prepared from plant parts of *Veratrum album*. The density of the original tincture ranges from 0.895 g/cm$^3$ to 0.905 g/cm$^3$. The dry residue ranges from 1.8% to 3.4%. The dry residue itself has a minimum content of alkaloids of 0.07%. These alkaloids comprise especially veratrine and gemerine.

(f) *Aconitum napellus*, D4

For preparing the original tincture, the fresh above-ground parts gathered at the beginning of blossoming time and root tubers of *Aconitum napellus L.* are used. Unlike the above-mentioned specification, the plant mass is extracted with 86% ethanol, the amount ($A_2$) of which is calculated according to the following formula:

$$A_2 = \frac{M \times T}{100} \text{ (kg)},$$

wherein
M is the weight of the plant mass in kg, and
T is the loss of the sample on drying in %.

The original tincture is a greenish-yellow, later brownish-yellow liquid having a typical smell. The relative density ranges from 0.930 g/cm$^3$ to 0.942 g/cm$^3$. The dry residue has to amount to at least 2.0%. Unlike the above-mentioned general potentiating specification, the 1st decimal dilution is prepared from 2 parts of original tincture and 8 parts of 30% ethanol. For preparing the 2nd decimal dilution (and analogously D3 and D4) part of the 1st decimal dilution is blended with 9 parts of 15% ethanol.

(g) *Arnica planta tota*, D4

For preparing the original tincture, the whole fresh blossoming plant of *Arnica montana L.* is used. Unlike the above-mentioned general specification, 43% ethanol is used for preparing the original tincture. The original tincture is a yellow liquid having a typical smell and a bitter taste. Its relative density ranges from 0.95 g/cm$^3$ to 0.969 g/cm$^3$. The dry residue amounts to at least 1.0%. The decimal dilutions are prepared as specified above for (f) Aconitum napellus.

(h) *Atropa belladonna*, D4

For preparing the original tincture, the whole fresh plant of *Atropa belladonna L.* gathered at the end of blossoming time is used without the lignified lower stem parts. The original tincture is prepared in the same way as specified above for Aconitum napellus. The original tincture is a brown liquid having a peculiar smell. Its relative density ranges from 0.932 g/cm$^3$ to 0.947 g/cm$^3$. The dry residue amounts to at least 1.4%. The essential components comprise atropine.

The liquid dilutions are prepared as specified above for Aconitum napellus.

(i) *Cinchona succirubra* (China), D2

For preparing the original tincture, the dried bark of younger trunks and older twigs of *Cinchona succirubra* PAVON as well as their varieties and hybrids are used. The original tincture is a reddish-brown liquid having an agreeably bitter taste and has a total alkaloid content of at least 0.45% and at most 0.50%, at least 30% and at most 60% thereof consisting of alkaloids of the quinine type. Unlike the above-mentioned specification, the original tincture is prepared from 1 part of a coarsely pulverized drug and 10 parts of 62% ethanol. The relative density of the original tincture ranges from 0.895 g/cm$^3$ to 0.908 g/cm$^3$. The dry residue has to amount to at least 2.4%.

(k) *Eucalyptus globulus*, D2

For preparing the original tincture, the dried leaves of *Eucalyptus globulus* LABILL are used, which comprise at least 1.5% of essential oil. The original tincture is prepared as specified above for Cinchona succirubra (China) with 86% ethanol. The original tincture is a yellowish-green to brownish-green liquid having a heavily aromatic smell and a slightly bitter, typical taste. Its relative density ranges from 0.833 g/cm³ to 0.848 g/cm³. The dry residue has to amount to at least 2.0%.

(l) Lycopodium, D4

For preparing the original tincture, ground spores of the club moss species *Lycopodium clavatum lycopodiacea* is used. The spores contain a fatty oil and traces of alkaloids. The relative density of the original tincture ranges from 0.83 g/cm³ to 0.84 g/cm³. The dry residue ranges from 1.7% to 2.4%.

(m) *Nux vomica*, D4

For preparing the original tincture, the dried seeds of *Strychnos nux vomica* are used. The components comprise in particular the alkaloids strychnine and prucine. The total alkaloid content ranges from 0.246% to 0.255%. The relative density of the original tincture ranges from 0.896 g/cm³ to 0.901 g/cm³. The dry residue ranges from 1.23% to 1.68%.

(n) Sulfur, D6

For preparing the solution (D4), 1 part of sulfur is refluxed with 10,000 parts of 86% ethanol for 1 h. The 5th decimal dilution is prepared with 86% ethanol and the 6th decimal dilution is prepared with 62% ethanol. The relative density of the solution D4 ranges from 0.828 g/cm³ to 0.833 g/cm³. This solution has to contain at least 0.009% and must not contain more than 0.011% of sulfur.

EXAMPLE 1

For preparing the preparation according to the present invention equal weight proportions of Euphorbia cyparissias D4, Clematis recta D2 and Mezereum D3 are mixed with each other. The finished preparation is a clear, slightly yellowish liquid having a typical ethanol smell. The preparation is administered in this form (pure) as drops. According to a typical dosage in human medicine 10 to 15 drops are administered twice to three times a day. It is recommended to drink some water after having taken the preparation so as to get rid of the slightly biting ethanol taste.

The following examples of cases—which have been selected from a multiplicity of similar cases—concern the successful use of the wart treatment according to Example 1 for treating children and young people (up to about 16 years). In the case of otherwise healthy children and young people one may assume that the immunologic system, i.e. the substantially responsible T-cell reaction and the B-lymphocyte production, are sufficiently active. However, the specific answer to the invaded papillomaviruses may cause difficulties. According to experience made over several years the controlled stimulation with the wart treatment according to Example 1 is quite sufficient in this case and causes the warts to disappear after a short time.

Case 1:

A six-year-old girl had both legs covered with warts. 10 drops of the wart treatment according to Example 1 were perorally administered to the girl three times a day. After ten days, the warts had disappeared entirely. No new warts appeared after the girl had ceased to take the treatment.

Case 2:

A seven-year-old boy had plantar warts on the foot soles; further, wart colonies spread over both knees. 15 drops of the wart treatment according to Example 1 were administered to the boy three times a day. After three weeks, the warts had disappeared completely and permanently.

Case 3:

Warts spread over both hand backs of an eight-year-old girl. 15 drops of the wart treatment according to Example 1 were administered three times a day. After six days, the warts had disappeared almost completely.

EXAMPLE 2:

For preparing a wart treatment composition according to the present invention, 0 8.3 g of Euphorbia cyparissias, D4
8.3 g of Clematis recta, D2
8.3 g of Mezereum, D3
8.3 g of Ranunculus, D3
7.2 g of Veratrum album, D4
7.2 g of Aconitum, D4 and
7.2 g of Arnica, D3
are mixed with each other.

This wart treatment is used and dosed in the same way as that according to Example 1.

As is apparent, the wart treatment according to Example 2, comprises in addition to the necessary components—*Euphorbia cyparissias, Clematis recta* and Mezereum—four components as selective components which likewise have an immunostimulating effect. The composition according to Example 2 is especially provided for adults. As the defensive power of the organism generally decreases with increasing age, the interaction of many immunostimulating substances has to be utilized to attain an improved overall constitution on the basis of which a controlled defence against papillomaviruses is possible.

The following examples of cases—which have been selected from a multiplicity of similar cases—concern the successful use of the wart treatment according to Example 2.

Case 4

A 25-year-old woman working as a consulting-room assistant had persistent warts on the back of the hand which could not successfully be treated by conventional, local therapy (dabbing-on of salicylic acid solution). The woman took 15 drops of the wart treatment according to Example 2 three times a day. After approximately twenty days, the back of the hand was smooth. The warts did not reappear after the woman had ceased to take the treatment.

Case 5

A 29-year-old woman had suffered for a long time from persistent nail bed warts. 15 drops of the wart treatment according to Example 2 were administered three times a day. After three weaks, the nail bed warts had disappeared.

Case 6

A 30-year-old man had contracted a single, painful plantar wart on the thumb and a further nail bed wart, which handicapped him considerably in his occupation as a mechanic. 15 drops of the wart treatment according to Example 2 were administered three times a day. A positive reaction could be noticed already after three days; the warts receded. After ten days, the warts had disappeared completely and permanently.

EXAMPLE 3

For preparing a wart treatment composition according to the present invention, 8.3 g of *Euphorbia cyparissias*, D4
8.3 g of *Clematis recta*, D2
8.3 g of Mezereum, D3
8.3 g of Ranunculus, D3
8.1 g of *Veratrum album*, D4
7.2 g of Aconitum, D4
7.2 g of Arnica, D3
7.2 g of *Atropa belladonna*, D4
7.2 g of *Cinchona succirubra* (China), D2
7.2 g of Eucalyptus, D2
8.3 g of Lycopodium, D4
7.2 g of *Nux vomica*, D4 and
8.3 g of sulfur, D6
were mixed with each other.

The total ethanol content of the preparation amounts to 67%. This wart treatment composition is used and dosed analogously to that according to Example 1. It comprises further immunostimulating additives. "Sulfur" additionally constitutes a non-specific stimulator which can increase cell oxidation and cancel a disorder of specific enzyme functions. Preferably, this treatment is provided for particularly persistent cases and for use in the veterinary field.

The following examples of cases—which have been selected from a multiplicity of similar cases—concern the successful use of the wart treatment according to Example 3.

Case 7

A 30-year-old woman had been suffering from a papillomatous finger wart, which had already conventionally been treated without success (salicylic acid preparations and fluorouracil). 15 drops of the wart treatment composition according to Example 3 were administered to this woman three times a day. After 14 days, the finger wart had disappeared.

Case 8

A 29-year-old woman had been suffering from nail bed warts which had already enclosed the entire groove of the nail bed of both thumbs and of the forefingers. Additionally severe, furrowed nail deformations had already occurred. After a first attempt to remove the warts surgically, the patient had refused any further such attempt because of the severe pain and the lack of success. For a period of two months comprising short interruptions the wart treatment according to Example 3 was administered to the woman in a dose of 10 drops twice a day. Thereupon, the warts disappeared.

Case 9

A 75-year-old woman had both hands and the forearms covered with plaques. For years the woman had been suspected of suffering from epidermodysplasia. The mobility of the fingers was greatly restricted due to extensive keratoses. An attempt to remove the plaques surgically failed. After the wart treatment according to Example 3 according to the present invention had been administered to the woman for six months (dose: 10 drops twice a day), the plaques had disappeared almost entirely.

Case 10

A 70-year-old woman had been suffering from a papillomatous wart on the ring finger. After two operations a great wart appeared again in the scar area. After the wart treatment according to Example 3 according to the present invention had been administered to the woman for two months (dose: 10 drops twice a day), the warts had disappeared.

Case 11

A 25-year-old man had been suffering from a wart in the palm; this wart was twice the size of a pea. After administration of the wart treatment according to Example 3 according to the present invention for fourteen days (dose: 10 drops twice a day), the wart disappeared.

Case 12

Numerous, very small warts appeared on the whole body of a 35-year-old man. Important immune parameters were determined independently; this determination confirmed a weakened immune status. 15 drops of the wart treatment according to Example 3 were administered to the patient three times a day. After three months even the last warts had disappeared. The success of the therapy was complete and permanent.

Case 13

Bursting warts having a diameter of approx. 4 cm and being due to severe secondary infection appeared on the forearms in the area between coronet joint and hock of an 8-year-old gelding. 5 ml of the wart treatment according to Example 3 according to the present invention were administered to the animal together with the oats twice a day. As a first reaction, healing from the edge could be noticed already after a few days. After four weeks, the hair had regrown, except for a smooth, healthy skin surface of a size of 0.5 cm$^2$.

I claim:

1. A perorally administrable pharmaceutic preparation for the treatment of warts by peroral administration, consisting of
   (a) 8.3 parts by weight of *Euphorbia cyparissias* extract, degree of dilution D3 to D6;
   (b) 8.3 parts by weight of Clematis extract, degree of dilution D2 to D4;
   (c) 8.3 parts by weight of Mezereum extract, degree of dilution D2 to D4;
   (d) 8.3 parts by weight of Ranunculus extract, degree of dilution D2 to D4;
   (e) 8.1 parts by weight of *Veratrum album* extract, degree of dilution D3 to D6;
   (f) 7.2 parts by weight of Aconitum extract, degree of dilution D3 to D6;
   (g) 7.2 parts by weight of Arnica extract, degree of dilution D2 to D4;

(h) 7.2 parts by weight of *Atropa belladonna* extract, degree of dilution D3 to D6;

(i) 7.2 parts by weight of *Cinchona succiruba* (China) extract, degree of dilution D2 to D4;

(k) 7.2 parts by weight of *Eucalyptus globulus* extract, degree of dilution D2 to D4;

(l) 7.2 parts by weight of Lycopodium extract, degree of dilution D3 to D6;

(m) 7.2 parts by weight of *Nux vomica* extract, degree of dilution D3 to D6; and (n) 8.3 parts by weight of sulfur, degree of dilution D4 to D6.

2. A wart removing composition for peroral administration which comprises liquid dilutions of:

(a) 0.5 to 2 parts by weight of *Euphorbia cyparissias* extract, degree of dilution D3 to D6;

(b) 0.5 to 2 parts by weight of Clematis recta extract, degree of dilution D2 to D4; and (c) 0.5 to 2 parts by weight of Mezereum extract, degree of dilution D2 to D4.

3. The wart removing composition of claim 2 which further comprises sulfur, degree of dilution D4 to D6.

4. The wart removing composition of claim 3 which further comprises at least one of the plant extracts selected from the group of:

(d) 0.5 to 2 parts by weight of Ranunculus extract, degree of dilution D2 to D4;

(e) 0.5 to 2 parts by weight of *Veratrum album* extract, degree of dilution D3 to D6;

(f) 0.5 to 2 parts by weight of Aconitum extract, degree of dilution D3 to D6; and (g) 0.5 to 2 parts by weight of Arnica extract, degree of dilution D2 to D4.

5. The wart removing composition of claim 3 which contains:

(a) 0.5 to 2 parts by weight of *Euphorbia cyparissias* extract, degree of dilution D3 to D6;

(b) 0.5 to 2 parts by weight of Clematis extract, degree of dilution D2 to D4;

(c) 0.5 to 2 parts by weight of Mezereum extract, degree of dilution D2 to D4;

(d) 0.5 to 2 parts by weight of Ranunculus extract, degree of dilution D2 to D4;

(e) 0.5 to 2 parts by weight of *Veratrum album* extract, degree of dilution D3 to D6;

(f) 0.5 to 2 parts by weight of Aconitum extract, degree of dilution D3 to D6; and (g) 0.5 to 2 parts by weight of Arnica extract, degree of dilution D2 to D4.

6. The composition of claim 2 wherein said liquid dilutions are of ethanolic plant extracts.

7. The wart removing composition of claim 2 which further comprises at least one of the plant extracts selected from the group of:

(d) 0.5 to 2 parts by weight of Ranunculus extract, degree of dilution D2 to D4;

(e) 0.5 to 2 parts by weight of *Veratrum album* extract, degree of dilution D3 to D6;

(f) 0.5 to 2 parts by weight of Aconitum extract, degree of dilution D3 to D6; and (g) 0.5 to 2 parts by weight of Arnica extract, degree of dilution D2 to D4.

8. The wart removing composition of claim 2 which contains:

(a) 0.5 to 2 parts by weight of *Euphorbia cyparissias* extract, degree of dilution D3 to D6;

(b) 0.5 to 2 parts by weight of Clematis extract, degree of dilution D2 to D4;

(c) 0.5 to 2 parts by weight of Mezereum extract, degree of dilution D2 to D4;

(d) 0.5 to 2 parts by weight of Ranunculus extract, degree of dilution D2 to D4;

(e) 0.5 to 2 parts by weight of *Veratrum album* extract, degree of dilution D3 to D6;

(f) 0.5 to 2 parts by weight of Aconitum extract, degree of dilution D3 to D6; and (g) 0.5 to 2 parts by weight of Arnica extract, degree of dilution D2 to D4.

9. A method for removing warts caused by papillomaviruses in a human or animal which comprises perorally administering to a human or animal having warts caused by papillomaviruses a composition comprising liquid dilutions of:

(a) 0.5 to 2 parts by weight of *Euphorbia cyparissias* extract, degree of dilution D3 to D6;

(b) 0.5 to 2 parts by weight of Clematis extract, degree of dilution D2 to D4;

(c) 0.5 to 2 parts by weight of Mezereum extract, degree of dilution D2 to D4.

10. The method of claim 9 wherein said composition further comprises sulfur, degree of dilution D4 to D6.

11. The method of claim 10 wherein said composition further comprises at least one of the following plant extracts selected from the group of:

(d) 0.5 to 2 parts by weight of Ranunculus extract, degree of dilution D2 to D4;

(e) 0.5 to 2 parts by weight of *Veratrum album* extract, degree of dilution D3 to D6;

(f) 0.5 to 2 parts by weight of Aconitum extract, degree of dilution D3 to D6; and (g) 0.5 to 2 parts by weight of Arnica extract, degree of dilution D2 to D4.

12. The method of claim 10 wherein said composition contains:

(a) 0.5 to 2 parts by weight of *Euphorbia cyparissias* extract, degree of dilution D3 to D6;

(b) 0.5 to 2 parts by weight of Clematis extract, degree of dilution D2 to D4;

(c) 0.5 to 2 parts by weight of Mezereum extract, degree of dilution D2 to D4;

(d) 0.5 to 2 parts by weight of Ranunculus extract, degree of dilution D2 to D4;

(e) 0.5 to 2 parts by weight of *Veratrum album* extract, degree of dilution D3 to D6;

(f) 0.5 to 2 parts by weight of Aconitum extract, degree of dilution D3 to D6; and (g) 0.5 to 2 parts by weight of Arnica extract, degree of dilution D2 to D4.

13. The method of claim 10 wherein said composition contains:

(a) 0.5 to 2 parts by weight of *Euphorbia cyparissias* extract, degree of dilution D3 to D6;

(b) 0.5 to 2 parts by weight of Clematis extract, degree of dilution D2 to D4;

(c) 0.5 to 2 parts by weight of Mezereum extract, degree of dilution D2 to D4;

(d) 0.5 to 2 parts by weight of Ranunculus extract, degree of dilution D2 to D4;

(e) 0.5 to 2 parts by weight of *Veratrum album* extract, degree of dilution D3 to D6;

(f) 0.5 to 2 parts by weight of Aconitum extract, degree of dilution D3 to D6; and (g) 0.5 to 2 parts by weight of Arnica extract, degree of dilution D2 to D4;

(h) 7.2 parts by weight of *Atropa belladonna* extract, degree of dilution D3 to D6;

(i) 7.2 parts by weight of *Cinchona succiruba* (China) extract, degree of dilution D2 to D4;
(j) 7.2 parts by weight of *Eucalyptus globulus* extract, degree of dilution D2 to D4;
(k) 7.2 parts by weight of Lycopodium extract, degree of dilution D3 to D6;
(l) 7.2 parts by weight of Nux vomica extract, degree of dilution D3 to D6; and
(m) 8.3 parts by weight of sulfur extract, degree of dilution D4 to D6.

14. The method of claim 9 wherein said composition further comprises at least one of the following plant extracts selected from the group of:
(d) 0.5 to 2 parts by weight of Ranunculus extract, degree of dilution D2 to D4;
(e) 0.5 to 2 parts by weight of *Veratrum album* extract, degree of dilution D3 to D6;
(f) 0.5 to 2 parts by weight of Aconitum extract, degree of dilution D3 to D6; and
(g) 0.5 to 2 parts by weight of Arnica extract, degree of dilution D2 to D4.

15. The method of claim 9 wherein said composition contains:
(a) 0.5 to 2 parts by weight of *Euphorbia cyparissias* extract, degree of dilution D3 to D6;
(b) 0.5 to 2 parts by weight of Clematis extract, degree of dilution D2 to D4;
(c) 0.5 to 2 parts by weight of Mezereum extract, degree of dilution D2 to D4;
(d) 0.5 to 2 parts by weight of Ranunculus extract, degree of dilution D2 to D4;
(e) 0.5 to 2 parts by weight of *Veratrum album* extract, degree of dilution D3 to D6;
(f) 0.5 to 2 parts by weight of Aconitum extract, degree of dilution D3 to D6; and
(g) 0.5 to 2 parts by weight of Arnica extract, degree of dilution D2 to D4.

16. The method of claim 9 wherein said liquid dilutions are of ethanolic plant extracts.

* * * * *